(12) United States Patent
Desroche et al.

(10) Patent No.: US 10,449,222 B2
(45) Date of Patent: Oct. 22, 2019

(54) **METHOD FOR PREVENTING AND/OR TREATING INFECTIONS, COLONISATIONS, OR ILLNESSES RELATED TO *STAPHYLOCOCCUS AUREUS*, *PSEUDOMONAS AERUGINOSA*, *STREPTOCOCCUS PYOGENES*, *ENTEROCOCCUS FAECIUM*, *ENTEROBACTER CLOACAE*, *PROTEUS MIRABILIS*, *BACTEROIDES FRAGILIS*, *STAPHYLOCOCCUS EPIDERMIDIS*, *PROPIONIBACTERIUM ACNES*, *CANDIDA ALBICANS* AND/OR *MALASSEZIA FURFUR***

(71) Applicant: Laboratoires Urgo, Chenove (FR)

(72) Inventors: Nicolas Desroche, Quetigny (FR); Patrice Arbault, Orlienas (FR); Jean Guzzo, Fontaine les Dijon (FR); Sandra Rodrigues, Crimolois (FR); Christelle Laurensou, Dijon (FR); Sylvain Mery, Arc sur Tille (FR); Laurent Apert, Dijon (FR)

(73) Assignee: LABORATOIRES URGO, Chenove (FR)

( * ) Notice: Subject to any disclaimer, the term of this patent is extended or adjusted under 35 U.S.C. 154(b) by 90 days.

(21) Appl. No.: 15/786,738

(22) Filed: Oct. 18, 2017

(65) Prior Publication Data

US 2018/0036356 A1 Feb. 8, 2018

Related U.S. Application Data

(62) Division of application No. 14/648,837, filed as application No. PCT/FR2013/053071 on Dec. 13, 2013, now abandoned.

(30) Foreign Application Priority Data

Dec. 17, 2012 (FR) ...................... 12 62128

(51) Int. Cl.
| | | |
|---|---|---|
| A61K 35/744 | (2015.01) | |
| A61K 35/747 | (2015.01) | |
| A61K 35/741 | (2015.01) | |
| A61K 36/06 | (2006.01) | |
| A61K 45/06 | (2006.01) | |
| C12R 1/25 | (2006.01) | |
| C12R 1/46 | (2006.01) | |
| C12R 1/225 | (2006.01) | |

(52) U.S. Cl.
CPC .......... *A61K 35/747* (2013.01); *A61K 35/741* (2013.01); *A61K 35/744* (2013.01); *A61K 36/06* (2013.01); *A61K 45/06* (2013.01); *C12R 1/225* (2013.01); *C12R 1/25* (2013.01); *C12R 1/46* (2013.01)

(58) Field of Classification Search
None
See application file for complete search history.

(56) References Cited

U.S. PATENT DOCUMENTS

2015/0366920 A1    12/2015    Desroche et al.

FOREIGN PATENT DOCUMENTS

| EP | 1312667 | 5/2003 |
|---|---|---|
| WO | 2004/052462 | 6/2004 |
| WO | 2008/074331 | 6/2008 |
| WO | 2010/056198 | 5/2010 |

OTHER PUBLICATIONS

International Search Report in PCT/FR2013/053071 dated Mar. 24, 2014.
K. Oki et al., "*Lactobacillus saniviri* sp. Nov. and *Lactobacillus senioris* sp. Nov., isolated from human faeces," Int. J. System. Evol. Microbiol., 62(pt3):601-607 (2012).
Teanpaisan et al., "Inhibitory effect of oral *Lactobacillus* against oral pathogens," Lett. Appl. Microbiol., 53(4)452-459 (2011).

*Primary Examiner* — Vera Afremova
(74) *Attorney, Agent, or Firm* — McAndrews, Held & Malloy, Ltd.

(57) ABSTRACT

The subject matter of the present invention is a bacterium or a mixture of bacteria having an antagonistic activity with respect to strains of *S. aureus*, *P. aeruginosa*, *Streptococcus pyogenes*, *Enterococcus faecium*, *Enterobacter cloacae*, *Proteus mirabilis*, *Bacteroides fragilis*, *Staphylococcus epidermidis*, *Propionibacterium acnes*, *Candida albicans* and/or *Malassezia furfur* as well as the use thereof in the treatment and/or prevention of infections or colonizations related to those pathogens. The invention pertains to care products containing one or more non-pathogenic antagonistic strains intended to prevent and/or treat infections or colonizations on skin, wounds, mucous membranes and appendages.

12 Claims, 6 Drawing Sheets

METHOD FOR PREVENTING AND/OR TREATING INFECTIONS, COLONISATIONS, OR ILLNESSES RELATED TO *STAPHYLOCOCCUS AUREUS, PSEUDOMONAS AERUGINOSA, STREPTOCOCCUS PYOGENES, ENTEROCOCCUS FAECIUM, ENTEROBACTER CLOACAE, PROTEUS MIRABILIS, BACTEROIDES FRAGILIS, STAPHYLOCOCCUS EPIDERMIDIS, PROPIONIBACTERIUM ACNES, CANDIDA ALBICANS* AND/OR *MALASSEZIA FURFUR*

This application is a divisional application of U.S. patent application Ser. No. 14/648,837 filed Jun. 1, 2015, which is a U.S. National Phase application of International Patent Application No. PCT/FR2013/053071 filed Dec. 13, 2013, which claims the benefit of priority to French Patent Application No. 1262128 file Dec. 17, 2012. The entire text of the aforementioned applications is incorporated herein by reference in its entirety.

The present invention relates to bacteria having antagonist activities (hereinafter referred to as "antagonistic bacteria") with respect to pathogenic bacteria or yeasts belonging to the genera and species *Staphylococcus aureus, Pseudomonas aeruginosa, Streptococcus pyogenes, Enterococcus faecium, Enterobacter cloacae, Proteus mirabilis, Bacteroides fragilis, Staphylococcus epidermidis, Propionibacterium acnes, Candida albicans* and/or *Malassezia furfur* and to the use thereof as an active ingredient or in a medical device, in particular in the treatment and/or prevention of colonization and/or infections related to these pathogenic bacteria or yeasts. The bacteria which are antagonistic with respect to pathogenic bacteria or yeasts have been selected for their abilities to inhibit the adhesion and the development and/or the proliferation of pathogenic bacteria or yeasts and thus to stabilize and/or regulate the ecosystem. The invention relates to care products containing one or more non-pathogenic antagonistic strains intended for the prevention or treatment of infections or colonizations on the skin, wounds, mucosae and superficial body growths.

*Staphylococcus aureus* and *Pseudomonas aeruginosa* are responsible for a certain number of pathological conditions, such as skin and mucosae infections, wound infections, in particular infections of chronic wounds (ulcers, diabetic wounds), burns and surgical wounds. These bacterial species are in particular known to be responsible for delayed healing. They are also involved in other pathological conditions, such as gastrointestinal, urinary and pulmonary infections, otitis or sinusitis.

*Pseudomonas aeruginosa*, otherwise known as pyocyanic bacillus, can, under certain conditions, be pathogenic. This very resistant bacterium is, with other gram-negative bacteria, increasingly often involved in nosocomial infections. This strain has the ability to become organized as a biofilm, which makes it all the more resistant to antibiotics. It is one of the most difficult bacteria to treat clinically. The mortality rate reaches 50% in vulnerable (immunodepressed) patients. It is a ubiquitous microorganism which is very resistant to numerous antiseptics, which is frequent in the hospital environment, and which leads to the appearance (because of its resistance to antibiotics) of actual hospital strains. It generates various forms of pathological condition: eye infection, wound infection (especially burns and surgical wounds), urinary infection (especially after catheters), gastrointestinal and lung infections (for example after bronchoscopy), inoculation meningitis, septicemia such as the terminal state of serious infections, or complication in patients subjected to an immunosuppressive treatment, leukemia patients, etc. It readily induces systemic infections in individuals who are immunodepressed (because of chemotherapy or by AIDS) and in burn victims and cystic fibrosis victims.

*Staphylococcus aureus* is the most pathogenic species of the *Staphylococcus* genus. It is responsible for food poisoning, suppurative localized infections and, in certain extreme cases, physical septicemia (graft, cardiac prostheses). The species proves to be an opportunistic pathogen in certain locations or under certain circumstances. It is a ubiquitous microorganism which has good resistance to natural purification mechanisms. *S. aureus* is also found in the commensal flora (in 15% to 30% of healthy individuals in the nasal fossae and the throat, it can also be found in small amounts in the digestive tract and often at the level of the perineum).

*S. aureus* has pathogenic capacities, in particular an invasive capacity, a capacity to multiply and to spread in the organism, and also a toxic capacity. *S. aureus* has a great capacity for developing antibiotic-resistant mutants (by way of example, mention may be made of methicillin-resistant *Staphylococcus aureus*, or MRSA, which is one of the main causes of nosocomial infections). As a result, it shares, with pyocyanic *bacillus*, the primary role in infections of hospital origin.

These pathogenic bacteria and yeasts have the capacity to adhere to surfaces and in particular to epithelial tissues and to develop in the form of biofilms in healthy or immunodepressed hosts. Biofilms are defined as complex assemblies of microorganisms (or microbial communities) which adhere to a biotic surface (living tissues, skin, etc.) or an abiotic surface (inert material such as silicone or steel) and are trapped in a matrix of organic polymers (Costerton et al., 1999, Dunne, 2002). These biofilms may thus be monospecific, i.e. compounds of a single bacterial or yeast species, or mixed when they are composed of several bacterial or yeast species.

The common treatment for infections related to the presence of pathogenic bacterial species is the use of antibiotics (penicillin, cephalosporin). However, the use of this approach presents a certain number of drawbacks:
 these antibiotics often have a considerable spectrum of action and may be responsible for an imbalance in terms of the commensal flora, which may subsequently result in colonization by pathogenic microorganisms;
 the bacteria are capable of acquiring capacities of resistance to these antibiotics;
 the resistance of bacteria in the form of biofilms is greatly increased compared with bacteria alone, also called planktonic cells.

Faced with the problems of multiple resistances of pathogenic microorganisms to antibiotics, there is an urgent need to find an alternative to this type of treatment.

One solution envisioned in order to prevent or treat infections of bacterial or yeast origin is the use of bacterial strains which are antagonistic with respect to pathogenic species. The term bacteriotherapy is then used. These antagonistic strains are capable, by virtue of their metabolism, of producing antimicrobial molecules and/or of interfering with the adhesion of pathogenic bacteria and yeasts and/or of disrupting cell communication between pathogenic bacteria and yeasts and/or of possessing angiogenic activities. They can also control inflammation (immunomodulatory properties). These bacteria form a positive biofilm at the surface of the skin, wounds, mucosae or superficial body growths, which can take hold temporarily and limit the implantation of pathogenic bacteria and yeasts.

This is particularly advantageous when the infection and/or the colonization is located on the skin and/or in a wound.

These antagonistic strains generally belong to the family of lactic acid bacteria. These strains have been isolated from various matrices and mainly from feces. The activities of these strains are widely used for the prevention and treatment of disorders at the level of the intestinal mucosa; the term probiotic bacteria is then used. Other applications at the level of the mucosa of the ear, nose and throat and of the urogenital mucosa have also been described. By way of example, mention may be made of patent EP 871 503 which relates to a diaper or sanitary napkin comprising microorganisms chosen from the genera *Lactobacillus curvatus*, *Lactobacillus plantarum* or *Lactococcus lactis* having antagonistic properties which allow them to combat strains of undesirable microorganisms present or forming in the absorbent article, or in the urogenital zone. Patent application WO 99/53932 relates to a composition for the treatment of otitis, comprising microorganisms chosen from *Streptococcus sanguis, Streptococcus oxalis* and *Streptococcus mitis*.

The applicant has particularly focused on the strains which are antagonistic with respect to the pathogenic strains *S. aureus* and *P. aeruginosa*.

One of the objects of the present invention also potentially consists in creating a transient positive biofilm at the surface of the skin, superficial body growths, mucosae and/or wounds, which prevents or limits the implantation of pathogens and the proliferation thereof.

The antagonistic bacteria according to the present invention are particularly advantageous for use thereof in pathological conditions involving the pathogenic species *S. aureus* and *P. aeruginosa*, such as gastrointestinal, urinary and pulmonary infections, otitis or sinusitis, wounds or pathological conditions involving colonization of wounds, of the skin, of superficial body growths or of mucosae.

The antagonistic bacteria according to the present invention are particularly advantageous for use thereof in the various types of wounds (chronic, acute, burns), but also in skin conditions (such as, for example, folliculitis, impetigo, eczema, boils, anthrax, whitlow, atopies, perleche, superinfections of lesions related to viruses such as the herpes virus or the chickenpox virus).

Indeed, a wound is a lesion subsequent to a trauma, causing a loss of skin or an opening of the skin. The healing process is set up in response to the formation of a wound.

The natural healing of a wound occurs mainly according to three successive phases, each of these phases being characterized by specific cell activities which bring about the progression of the repair process according to precise chronological sequences: the inflammatory phase, the granulation phase (or proliferative phase), and the scar formation phase.

The rapidity and the quality of the healing of a wound depend on the general condition of the affected organism, on the etiology of the wound, on the condition and the location of the wound, on the possible occurrence of an infection, and also on genetic factors possibly predisposing to healing disorders. Torn or cut skin can no longer act as a barrier against microbes, which can then penetrate into the organism, causing an infection.

Bacteria and yeasts are inevitably present in wounds, this is natural colonization.

According to the amount of bacteria and/or of yeasts, the bacterial and/or yeast species present and the response of the organism, a distinction is made between colonization, local infection and infection.

Colonization is the presence of a certain amount of bacteria and/or of yeasts within the wound without this leading to an inflammatory response. After multiplication of the microorganisms on the wound, and adhesion thereof to epithelial cells, an equilibrium is established between the patient and the microbial flora thereof. The microorganisms remain at the surface of the wound and adhere thereto so as to form a biofilm. From a quantitative point of view, colonization is characterized by an amount of microorganism of less than $10^5$ bactreria/mm$^3$. If the amount of bacteria and/or of yeasts exceeds this number, some authors cite critical colonization, then strictly local superficial infection in the presence of considerable bacterial and/or yeast colonization. This considerable presence of bacteria and/or of yeasts is detrimental to the correct operating of the healing process and induces delayed healing.

The term "infection" will be used when the presence of the bacterial and/or yeast microorganisms leads to a locoregional inflammatory response and the appearance of general signs with clinical signs which reflect tissue invasion by the microorganisms present (large amount of the microorganisms present, bacterial virulence, decrease in immune defense mechanisms of the patient). The infection is characterized by the locoregional and general clinical signs.

Said infection can result in wound extension with exposure of underlying anatomical structures such as ligaments or bones.

Bacterial colonization does not require particular therapeutic approaches, whereas an infection requires the setting up of local and general antibacterial treatments.

The infection is generally the determining factor in the non-healing or delayed healing of wounds, directly or indirectly. Any bacterial and/or yeast contamination of a wound increases the inflammation.

This may be beneficial in the case of moderate contamination (inevitable in the case of an open wound), but becomes deleterious in the case of infection of the wound which results in delayed healing.

Thus, the immediate complication of healing is first and foremost the infection which prevents the initiation of the healing process from being set up; a wound is considered to be infected when the amount of bacteria and/or yeasts present in the wound hinders the healing process or worsens the wound.

In this case, the healing, termed second intention healing, usually requires the use of dermatological medicaments and of surgical tools (surgical knife, curette, etc.). In the case of a leg ulcer, for example, it is necessary to disinfect the wound beforehand with antiseptics (such as chlorhexidine or hexamidine) and to clean the wound, which consists in removing the debris and the excess secretion, either by means of a surgical act or using proteolytic medicaments, i.e. medicaments of which the purpose is to destroy the strips of dead skin which contaminate the wound. Among the active agents commonly used for treating wound infections, mention may also be made of silver, copper, octenidine, iodine, PHMB (polyhexamethylene biguanide) and honey.

However, antibacterial agents and/or antiseptics are not recommended in wounds. The effectiveness of these active agents, from the viewpoint of their mechanisms of action, is short lived, they are inactivated by organic substances, they may be cytotoxic with respect to cell components, they have a broad spectrum, and, consequently, they will not only attack the pathogenic bacteria, but will also destroy the commensal flora. Furthermore, a certain number of bacterial strains have developed a resistance to antiseptics/antibacterial agents.

There is therefore a need to have active agents which are effective in the treatment and/or prevention of wound infections or colonizations by bacteria and/or yeasts, which are efficient, easy to use and non-invasive.

One solution envisioned in order to prevent or treat infections or colonizations of bacterial origin and/or due to yeasts at the level of the skin, wounds, mucosae and/or superficial body growths is the use of bacterial strains which are antagonistic with respect to pathogenic strains. These strains are capable, by virtue of their metabolism, of producing antimicrobial molecules and/or interfering with the adhesion of pathogenic bacteria and/or yeasts. These bacteria can also form a positive biofilm at the surface of the skin, the wound, the mucosae or the superficial body growths, which can be established temporarily and limit the implantation of pathogenic bacteria and/or yeasts.

These antagonistic strains generally belong to the family of lactic acid bacteria and/or have been isolated from the commensal flora of the mucosae of human beings. The activities of these strains are widely used for the prevention and treatment of disorders at the level of the intestinal mucosa, of the ENT mucosa and of the vaginal mucosa. Such strains are described in WO 96/38159, WO 00/61201, EP 1 140 226, EP 1 461 012 and WO 2006/013441.

The antagonistic effect of these strains is due to various mechanisms, such as:
  nutritional competition for carbonaceous and/or nitrogenous substrates;
  production of antimicrobial molecules, such as lactic acid, hydrogen peroxide ($H_2O_2$), reducing molecules or bacteriocins;
  adhesion competition for the binding sites on the mucosae (barrier effect);
  production of biosurfactants;
  inhibition or disruption of cell communication between the various bacterial species;
  immunomodulatory activities enabling the stimulation of local and systemic immunity.

The applications using probiotic strains on the skin and wounds also generally make use of one of the activities previously described.

Mention may thus be made of applications concerning angiogenic effects of probiotic strains of *Lactobacillus acidophilus* ATCC 4356 and ATCC 43121, and *Bacillus polyfermenticus*, at the level of the skin and the intestinal mucosa (Halper et al., 2003, Im et al., 2009). Probiotic strains of *Bifidobacterium longum* neuter, of *Lactobacillus paracasei* CNCM 1-2116, of *Lactobacillus johnsonii* La1 and of *Vitreoscilla filiformis*, in topical forms, have also been used to regulate inflammation phenomena and dysregulations at the level of the skin (Gueniche et al., 2006, Gueniche et al., 2008a, Gueniche et al., 2008b, Gueniche et al., 2008c, Gueniche et al., 2008d, Gueniche et al., 2009, Gueniche et al., 2010). In the context of these applications, the authors emphasize the immunomodulatory capacity of the strains. Such strains are described in patent applications EP 1 593 382 and WO 2006/037922.

The use of a strain of *Lactobacillus plantarum* ATCC 10241 has been described for limiting the growth of *Pseudomonas aeruginosa* and the formation of biofilms by this strain by releasing signal molecules which disrupt cell communication (or quorum sensing). The direct application of a piece of gauze impregnated with a culture of this strain, on burn models in rats and on human burns, has made it possible to demonstrate its effectiveness (Peral et al., 2009, Valdez et al., 2005). The immunomodulatory capacity of this strain with respect to neutrophils and leukocytes has also been exploited for treating chronic wounds (diabetic wounds, venous ulcers) and for reducing inflammation caused by *P. aeruginosa* (Peral et al., 2010, Ramos et al., 2010, Ramos et al., 2012). A formulation of this strain in an alginate film has been described by Brachkova et al. (Brachkova et al., 2011) for the prevention of burn infections by *P. aeruginosa*.

A strain of *Lactobacillus fermentum* RC-14 has demonstrated notable capacities for inhibiting *Staphylococcus aureus* adhesion and limiting infections related to this microorganism at the level of surgical implants (Gan et al., 2002). This antimicrobial effect has been attributed to the release of a biosurfacant.

The effectiveness of several strains of *Lactobacillus* and *Bifidobacterium* isolated from different sources, in the prevention and treatment of methicillin-resistant *Staphylococcus aureus*, has also been demonstrated in a study by H. Sikorska et al., 2013.

The inhibition of the growth of *Staphylococcus epidermidis* and *Propionibacterium acnes* by strains of *Lactobacillus reuteri* (KCTC 3594, KCTC 3678 and KCTC 3679) has been demonstrated (Kang et al., 2012).

The effect of the bacteriocins produced by *Lactococcus* sp. HY 449 against inflammatory bacteria of the skin, such as *Staphylococcus epidermidis* ATCC 12228, *Staphylococcus aureus* ATCC 65389, *Streptococcus pyogenes* ATCC 21059 and *Propionibacterium acnes* ATCC 6919, has been demonstrated (Ho et al., 2006).

Dressings or fabrics calling for the use of probiotic strains (lactic acid bacteria of *Bacillus coagulans*) have already been described (U.S. Pat. No. 7,025,974 and WO 2008/074331). The effectiveness of these formulations is based solely on the use of bacterial strains capable of producing lactic acid as principal broad-spectrum antimicrobial agent.

The objective of the present invention is to provide novel active agents based on bacteria which are antagonistic with respect to the pathogenic bacteria *Staphylococcus aureus* and/or *Pseudomonas aeruginosa*, and which are effective in the treatment and/or prevention of colonization and/or infections related to these pathogenic bacteria, in particular at the level of the skin, wounds, mucosae and superficial body growths. In addition, these active agents can be administered directly in contact with the skin, wounds, mucosae and superficial body growths, or can easily be incorporated into compositions, in particular compositions suitable for topical application, and are non-invasive.

In an innovative manner, the antagonistic bacteria have been preselected on the basis of several criteria: (i) their capacities to inhibit the growth of pathogenic organisms, namely *S. aureus* and *P. aeruginosa*, (ii) their capacities to adhere and to form a positive biofilm on collagen and epidermis, (iii) their capacities to limit the adhesion of pathogenic microorganisms on matrices containing collagen and (iv) their capacities to limit the inflammatory reaction (TNF-α production by macrophages).

These bacteria are capable of developing a barrier effect at the level of the skin, wounds, mucosae and superficial body growths and thus of preventing and limiting the risks of colonizations and infections.

The inventors have been particularly interested in selecting strains which are antagonistic mainly with respect to the

*S. aureus* and *P. aeruginosa*, which are the pathogenic species predominantly involved in infections, in particular nosocomial infections.

Additionally, the inventors have selected bacterial strains which, in addition to inhibiting strains of *S. aureus* and *P. aeruginosa*, inhibit the development of other pathogenic species, such as *Streptococcus pyogenes, Enterococcus faecium, Enterobacter cloacae, Proteus mirabilis, Bacteroides fragilis, Staphylococcus epidermidis, Propionibacterium acnes, Candida albicans* and *Malassezia furfur*. These microorganisms are more particularly involved in wound and skin infections.

*Propionibacterium acnes* is an anaerobic gram-positive *bacillus* which grows relatively slowly and is normally present in the skin, the hair and the mucosae. It is responsible for acne.

The bacterium is widely present in the skin flora of most adults in good health, but it is also responsible for postoperative infections, which, in particular in the case of the presence of an implant, are potentially severe: central nervous system infections, endophthalmitis, endocarditis, infections of the ENT and pulmonary sphere, spondylodiscitis, peritonitis and osteoarticular infections.

*Staphylococcus epidermidis* is a commensal bacterium of the skin in virtually 100% of human beings; its lipolytic properties allow it to prosper in sebum. It is normally harmless, but it causes authentic infections in patients whose immune system is compromised or patients who have catheters or prostheses. These may be dermatological infections and nasal infections, such as sinusitis or else urinary infections in women and more rarely in men. These bacteria have the capacity to produce biofilms which allow them to adhere to the surfaces of medical prostheses.

*Candida albicans* manifests itself differently according to its location. In immunocompetent patients (i.e. whose defense system is effective, unlike immunodepressed patients), it appears in the form of thrush in the buccal cavity, redness and itching on the skin, essentially in the folds, which are warm and moist areas favorable to the development of yeast, and small local genital inflammations such as urethritis in human beings or vulvovaginitis with whitish discharge and itching in women.

*Malassezia furfur* is a yeast involved mainly in seborrheic dermatitis which is a common inflammatory skin dermatosis (observed in 3% to 5% of the population). It presents in the form of red plaques, covered with fatty and yellowish squamae, which are more or less prurigineous, predominant in the zones rich in sebaceous glands, the seborrheic zones. On the face, the topography of the lesions is suggestive: grooves between the nose and the lips, root of the eyebrows, scalp, wings of the nose, folds of the pinnae, concha of the ears, external auditory canals. On the scalp, frequent involvement results in a more or less seborrheic dandruff condition. On the trunk, two common zones are noted in humans: the sternum and the region between the two shoulder blades.

It is encountered both in adults and infants (of less than 3 months), in whom it manifests itself through the conventional "cradle cap" in the scalp and erythema on the buttocks. In adults, this pathological condition is observed especially on subjects between 20 and 40 years of age. Men are more frequently affected than women. In women, the development is observed more particularly at the time of the menopause. The pathological condition of multifactorial inflammatory origin is not contagious and can evolve through attacks triggered most commonly by stress or pollution and a lack of sun.

The cause is unknown, but a microscopic fungus is thought to play a role in conditions likely to produce a particular immunoallergy.

*Pityriasis versicolor* is a superficial mycosis, related to the proliferation on the skin of *Malassezia furfur*. This yeast normally lives at the surface of the skin, but, in certain situations, it multiplies at great speed and causes these small brown or discolored marks. This fungus has a liking particularly for oily skin, lying on the thorax, but also on the neck and the shoulders, on the upper back and on the upper limbs, rarely on the lower limbs.

A subject of the present invention is therefore a bacterium chosen from the strains of *Lactobacillus saniviri* also denoted in the present application by F3C5p (registered on Jul. 12, 2012, under No. CNCM 1-4650 at the Collection Nationale de Cultures de Microorganismes [National Collection of Microorganism Cultures], Institut Pasteur, 25 rue du Docteur Roux, 75724 Paris Cedex 15, France, hereinafter denoted "CNCM"), *Lactobacillus salivarius* also denoted in the present application by F50C2p, F52C3p and F41C3p (registered respectively under Nos. CNCM 1-4651, CNCM 1-4652 and CNCM 1-4653 at the CNCM), *Streptococcus mitis* also denoted in the present application by F3C2v (registered on Jul. 12, 2012, under No. CNCM 1-4654 at the CNCM) and *Lactobacillus pentosus* or *plantarum* also denoted in the present application by L1C1 (registered on Jul. 12, 2012 under No. CNCM 1-4655 at the CNCM). These bacteria are called "bacteria according to the invention" in the present application.

A subject of the present invention is also a bacterium according to the invention for use as an immunomodulator.

The subject of the present invention is also the use of such a bacterium as an active ingredient or as a medical device or as a cosmetic or else as a food supplement. The bacterium according to the invention may also be used as an active ingredient in a medicament, in a medical device, in a cosmetic or in a food supplement.

The present invention is also directed toward a bacterium according to the invention for use in the treatment and/or prevention of colonization and/or infections related to at least one bacterium or one yeast chosen from *P. aeruginosa, S. aureus, S. pyogenes, E. faecium, E. cloacae, P. mirabilis, B. fragilis, Staphylococcus epidermidis, Propionibacterium acnes, Candida albicans* and *Malassezia furfur*.

Preferentially, the present invention is directed toward a bacterium according to the invention for use in the treatment and/or prevention of colonization and/or infections related to *P. aeruginosa* and/or *S. aureus*.

The present invention relates more particularly to the treatment and/or prevention of wound and skin colonization and/or infections by pathogenic bacteria or yeasts.

The term "treatment" of or "treating" an infection or a colonization means reducing and/or inhibiting the development of this infection or colonization.

The term "prevention" of or "preventing" an infection or colonization means reducing and/or avoiding the appearance of the symptoms of the infection or colonization.

The expression "infection or colonization of wounds" is intended to mean an infection or a colonization chosen from diabetic foot ulcers, leg ulcers of arterial origin, leg ulcers of venous origin, bedsores, whitlow, infections related to acute wounds, infections related to traumatic wounds, such as wounds caused by severing, penetrating wounds, wounds caused by thermal or caustic agents and burns; and infections related to post-operative wounds, such as simple sutured wounds of a surgical incision, complex sutured wounds after skin excision, surgical dermabrasions and non-suturable wounds requiring second-intention healing.

The bacterium according to the invention can be incorporated into a composition, for instance a medical device. For the purposes of the present invention, the term "medical device" is intended to mean prostheses, catheters, dressings, ostomy bags, surgical drapes, urinary catheters, endotracheal tubes, tympanostomy tubes, bandages, support bandages, orthopedic and breast implants, contact lenses, intrauterine devices, or else materials for sutures.

A subject of the present invention is also a composition comprising at least one bacterium according to the invention. Said composition comprises, in an acceptable medium, at least one bacterium according to the invention. The term "acceptable medium" is intended to mean a medium that is compatible with the skin, wounds, mucosae and superficial body growths.

The composition according to the invention, or the bacterium according to the invention, may be administered topically, orally or parenterally.

Preferably, such a composition or such a bacterium is suitable for topical application to the skin, wounds, superficial body growths or mucosae, such as the nose and throat, urogenital, digestive or respiratory mucosa. The composition may thus be directly applied to the skin, wounds or mucosae.

The term "topical application" is intended to mean application to the skin, wounds, mucosae and/or superficial body growths.

The composition according to the invention preferably comprises $10^3$ to $10^{12}$ bacteria, preferably $10^6$ to $10^{11}$.

The topical composition may be in liquid, paste or solid form, and more particularly in the form of a salve, a cream, a milk, an ointment, a powder, an impregnated pad, a syndet, a wipe, a solution, a gel, a spray, a foam, a suspension, a lotion, a stick, a shampoo or washing base. It may also be in the form of a suspension of microspheres or nanospheres or of lipid or polymeric vesicles or of microcapsules or of a polymeric patch and a hydrogel for controlled release. This composition for topical application may be in anhydrous form, in aqueous form or in emulsion form.

The parenteral composition may be in the form of a solution for subcutaneous injection (injectable solution).

The oral composition may be in the form of a solution, a powder, a gel capsule or a tablet, or may be integrated into a food product, such as a dairy product.

The bacterium according to the invention may be incorporated into the composition in the form of an inactivated cell, in particular inactivated by heat, by UV radiation or by any other process. It may also be incorporated in the form of a living cell which may be encapsulated or nonencapsulated, immobilized or nonimmobilized, and lyophilized or nonlyophilized, or else in the form of a cell extract. It may also be a cell lysate or any other type of presentation known to those skilled in the art.

Preferentially, the antagonistic bacteria used in the context of the present invention, or a galenic formulation containing them, will be applied directly to the wound, either in the form of a topical composition, or integrated into a synthetic or nonsynthetic matrix which is part of the composition of a dressing.

In this embodiment, the bacteria are formulated in a dressing, or else formulated in a composition which is itself included in a dressing or may be included at the time of application of the dressing. The dressing according to the invention therefore comprises at least one bacterium according to the invention, or at least one composition according to the invention.

The antagonistic bacteria according to the invention or the compositions according to the invention containing them may be incorporated into any component of the structure of a dressing, with the proviso that said bacteria can directly or indirectly come into contact with the surface of the wound.

Preferably and in order to promote a rapid action, the bacterium (or a composition according to the invention containing it), will be incorporated into the layer of the dressing which comes into contact with the wound, or will be deposited on the surface of the dressing which comes into contact with the wound.

Advantageously, the bacterium (or a composition according to the invention containing it) may thus be deposited, in a continuous or discontinuous manner, on the surface intended to come into contact with the wound:
  either in liquid form, for example by spraying a solution or suspension containing it;
  or in solid form, for example by sieving a powder containing it.

For the purposes of the present invention, the term "dressing" is intended to denote all types of dressings used for the treatment of wounds. Typically, a dressing comprises at least one adhesive or nonadhesive layer or matrix.

The layer or surface which comes into contact with the wound may consist of any material or combination of materials normally used for this purpose in the dressings field. Among these materials, mention may be made of absorbent foams, in particular polyurethane-based hydrophilic foams; textile materials, in particular nonwovens based on absorbent or superabsorbent fibers; hydrogels; or a combination of these materials; an absorbent or nonabsorbent adhesive material; an adherent or nonadherent interface structure.

Generally, the galenic or the structure of the dressing may be adjusted in order to obtain a specific release profile for the bacterium, which is rapid or delayed, as required.

Thus, the bacterium (or a composition according to the invention containing it) may be integrated into any type of existing dressing, such as, without these examples being limiting:
  alginates such as, by way of examples, the products sold under the names Urgosorb® by Laboratoires Urgo or Melgisorb® by Mölnlycke;
  hydrocellular products such as, by way of example, the products sold under the names Urgotul Absorb® by Laboratoires Urgo or Tielle by Systagenix;
  hydrocolloid dressings such as, by way of examples, the products sold under the names Algoplaque® by Laboratoires Urgo and Comfeel® by Coloplast;
  hydrogels such as, by way of example, the products sold under the names Urgo Hydrogel® by Laboratoires Urgo and Intrasite Gel® by Smith & Nephew;
  liquid dressings such as, by way of example, the products sold under the names Urgo Crevasses by Laboratoires Urgo or Nexcare® by 3M.

Of course, the amount of bacterium or bacteria used in the galenic formulation or in the dressing will be adjusted according to the desired kinetics and also the specific constraints related to its nature, solubility, heat resistance, etc.

In the context of its use in a dressing component, the bacterium or bacteria according to the invention will be incorporated in an amount such that the amount of bacteria released into the wound exudates is between 0.001 g/l and 50 g/l, and preferably between 0.01 and 10 g/l.

According to the galenics chosen, the use of the dressing may require prior impregnation or hydration of the dressing with a solution, for instance physiological saline, in order to activate the antagonistic bacteria.

The composition according to the invention may comprise one or more antagonistic strains, optionally combined with at least one compound chosen from probiotics, prebiotics and yeasts. Among the prebiotics, mention may be made, by way of example, of fructans such as inulin, fructooligosaccharides or trans-galactooligosaccharides, or else long-chain or branched-chain sugars.

The bacterium according to the invention may also be combined with active agents in particular chosen from antifungal agents, painkillers, anti-inflammatories, agents which promote healing, moisturizing agents, keratolytic agents, restructuring active agents, and anesthetics.

In particular, the active agents which can be introduced into the composition according to the invention may be chosen from:
- antifungal agents such as polyenes, nystatin, amphotericin B, natamycin, imidazole compounds (miconazole, ketoconazole, clotrimazole, econazole, bifonazole, butoconazole, fenticonazole, isoconazole, oxiconazole, sertaconazole, sulconazole, thiabendazole, tioconazole), triazole compounds (fluconazole, itraconazole, ravuconazole, posaconazole, voriconazole), allylamines, terbinafine, amorolfine, naftifine, or butenafine; flucytosine (antimetabolite), griseofulvin, caspofungin or micafungin;
- painkillers such as paracetamol, codeine, dextropropoxyphene, tramadol, morphine and its derivatives, corticoids and derivatives;
- anti-inflammatories such as glucocorticoids, non-steroidal anti-inflammatories, aspirin, ibuprofen, ketoprofen, flurbiprofen, diclofenac, aceclofenac, ketorolac, meloxicam, piroxicam, tenoxicam, naproxene, indomethacin, naproxcinod, nimesulide, celecoxib, etoricoxib, parecoxib, rofecoxib, valdecoxib, phenylbutazone, niflumic acid or mefenamic acid;
- active agents which promote healing, such as retinol, vitamin A, vitamin E, N-acetyl-hydroxyproline, *Centella asiatica* extracts, papain, silicones, thyme, niaouli, rosemary and sage essential oils, hyaluronic acid, synthetic polysulfated oligosaccharides having 1 to 4 monosaccharide units, such as sucrose octasulfate potassium salt, sucrose octasulfate silver salt or sucralfate, or allantoin;
- moisturizing agents such as hyaluronic acid, urea, glycerol, fatty acids, aquaporin modulators, vegetable oils, chitosan, certain sugars, including sorbitol, butters and waxes;
- keratolytic agents such as salicylic acid, zinc salicylate, ascorbic acid, alpha-hydroxy acids (glycolic acid, lactic acid, malic acid, citric acid, tartaric acid), silver maple, sour cherry or tamarind extracts, urea, the topical retinoid Keratoline® (Sederma), proteases obtained by fermentation of *Bacillus subtilis*, or the product Linked-Papain® (SACI-CFPA);
- restructuring active agents (for example, restructuring active agents for superficial body growths), such as silica derivatives, vitamin E, chamomile, calcium, horsetail extract or silk lipester;
- anesthetics such as benzocaine, lidocaine, dibucaine, pramoxine hydrochloride, bupivacaine, mepivacaine, prilocaine, or etidocaine.

By way of illustration and without any limiting nature, various examples of use of the bacteria according to the invention will be given which make it possible to demonstrate the antibacterial activities of the antagonist strains according to the invention.

EXAMPLE 1

Antimicrobial activities of the bacterial strains *Lactobacillus* saniviri F3C5P (CNCM 1-4650), *Lactobacillus salivarius* F50C2P (CNCM 1-4651), *Lactobacillus salivarius* F52C3P (CNCM 1-4652), *Lactobacillus salivarius* F41C3P (CNCM 1-4653), *Streptocuccus mitis* F3C2V (CNCM 1-4654) and *Lactobacillus salivarius* or *plantarum* L1C1 (CNCM 1-4655)

The *Lactobacillus* saniviri F3C5p (CNCM 1-4650), *Lactobacillus salivarius* F50C2p, F52C3p and F41C3p (respectively CNCM 1-4651, CNCM 1-4652 and CNCM 1-4653), *Streptococcus mitis* F3C2v (CNCM 1-4654) and *Lactobacillus pentosus* or *plantarum* L1C1 (CNCM 1-4655) bacteria were cultured in Man Rogosa Sharpe (MRS) medium for 16 hours, at 37° C. and under anaerobic conditions. Drops of 10 µl of these cultures were deposited at the surface of Tryptic Soy Agar (TSA) media preinoculated in the body of the agar media with $10^6$ to $10^7$ cells of methicillin-resistant *Staphylococcus aureus* (MRSA) ATCC 43300 or *Pseudomonas aeruginosa* ATCC 9027 or *Bacteroides fragilis* ATCC 23745 or *Enterobacter cloacae* CIP 105132 or *Enterococcus faecium* ATCC 700221 or *Proteus mirabilis* CIP 107283 or *Streptococcus pyogenes* ATCC 19615 or *Staphylococcus epidermidis* ATCC 14990 or *Propionibacterium acnes*

ATCC 6919 or *Candida albicans* ATCC 10231 or *Malassezia furfur* ATCC 14521, per ml of agar medium.

A negative control was carried out by depositing 10 µl of sterile MRS medium.

The plates were incubated under anaerobic conditions at 37° C. for 24 and 48 hours. After incubation, the diameter of the inhibition halos formed around the drops (in mm) was measured.

The results of this experiment are shown in table 1.

Figure 1:
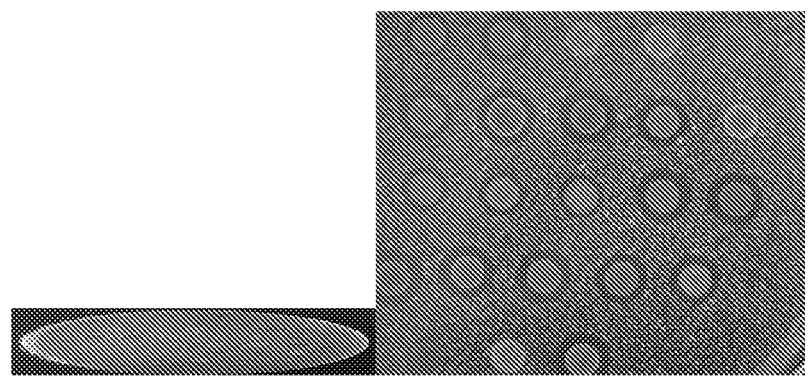
FIG. 1 represents the inhibition halos observed after contact of the bacteria according to the invention with pathogenic bacteria on agar medium after 48 hours of incubation.
Figure 2:
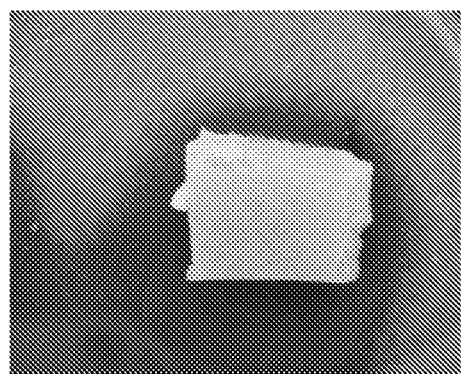
FIG. 2 represents an inhibition halo formed after contact with the bacteria according to the invention, incorporated into a dressing, with pathogenic bacteria on agar medium after 48 hours of incubation.

The sign "−" indicates an absence of inhibition halo, a sign "+" indicates an inhibition halo with a diameter of less than 1 mm, a sign "++" indicates an inhibition halo with a diameter of between 1 mm and 3 mm and a sign "+++" indicates an inhibition halo with a diameter of greater than 3 mm No inhibition halo was demonstrated with the negative control. Inhibition halos were observed with the 3 strains of bacteria tested (cf. FIG. 1).

crobial activity is demonstrated by the presence of an inhibition halo. After incubation, the inhibition halos are visible around the dressings impregnated with the bacteria *Lactobacillus* saniviri F3C5p, *Lactobacillus salivarius* F50C2p, *Lactobacillus salivarius* F52C3p, *Lactobacillus salivarius* F41C3p, *Streptococcus mitis* F3C2v and *Lactobacillus pentosus* or *plantarum* L1C1 (cf. FIG. 2). No inhibition halo is visible around the dressings impregnated with the MRS medium.

EXAMPLE 3

Capacities of the strains according to the invention to adhere on collagen

Tests for adhesion of the *Lactobacillus* saniviri F3C5p, *Lactobacillus salivarius* F50C2p, *Lactobacillus salivarius*

TABLE 1

Results of the tests of antimicrobial activity of the strains *Lactobacillus saniviri* F3C5p (CNCM I-4650), *Lactobacillus salivarius* F50C2p (CNCM I-4651), *Lactobacillus salivarius* F52C3p (CNCM I-4652), *Lactobacillus salivarius* F41C3p (CNCM I-4653), *Streptococcus mitis* F3C2v (CNCM I-4654) and *Lactobacillus pentosus* or *plantarum* L1C1 (CNCM I-4655)

| Strains | S. aureus ATCC 43300 | P. aeruginosa ATCC 9027 | B. fragilis ATCC 23745 | E. cloacae CIP 105132 | P. mirabilis CIP 107283 | E. faecium ATCC 700221 | S. pyogenes ATCC 19615 | Staphylococcus epidermidis ATCC 14990 | Propionibacterium acnes ATCC 6919 | Candida albicans ATCC 10231 | Malassezia furfur ATCC 14521 |
|---|---|---|---|---|---|---|---|---|---|---|---|
| L. saniviri F3C5p (CNCM I-4650) | +++ | + | +++ | ++ | ++ | +++ | +++ | +++ | +++ | + | +++ |
| L. salivarius F50C2p (CNCM I-4651) | ++ | + | ++ | + | + | ++ | +++ | +++ | +++ | − | − |
| L. salivarius F52C3p (CNCM I-4652) | ++ | ++ | ++ | + | ++ | ++ | +++ | +++ | +++ | − | − |
| L. salivarius F41C3p (CNCM I-4653) | + | − | − | + | + | − | +++ | ++ | +++ | − | − |
| S. mitis F3C2v (CNCM I-4654) | ++ | − | +++ | − | ++ | +++ | ++ | − | +++ | − | ++ |
| Lactobacillus sp. L1C1 (CNCM I-4655) | + | − | ++ | + | + | + | ++ | + | +++ | − | − |

EXAMPLE 2

Antimicrobial activities of the bacterial strains *Lactobacillus* saniviri F3C5P (CNCM 1-4650), *Lactobacillus salivarius* F50C2P (CNCM 1-4651), *Lactobacillus salivarius* F52C3P (CNCM 1-4652), *Lactobacillus salivarius* F41C3P (CNCM 1-4653), *Streptococcus mitis* F3C2V (CNCM 1-4654) and *Lactobacillus pentosus* or *plantarum* L1C1 (CNCM 1-4655) after incorporation into a dressing The F3C5p, F50C2p, F52C3p, F41C3p, F3C2v and L1C1 bacteria were cultured in Man Rogosa Sharpe (MRS) medium for 16 hours, at 37° C. and under anaerobic conditions. Pieces of dressings (1 cm×1 cm) composed of polyurethane foam and of a lipido-colloid mesh were impregnated with 500 µl of the culture of bacteria according to the invention (concentration of between $10^9$ and $10^{10}$ CFU·ml$^{-1}$) and deposited at the surface of Tryptic Soy Agar (TSA) media preinoculated in the body of the agar media with $10^6$ to $10^7$ cells of *Staphylococcus aureus* MRSA ATCC 43300 or *Pseudomonas aeruginosa* ATCC 9027. A negative control was carried out by depositing 500 µl of sterile MRS medium.

The plates were incubated under anaerobic conditions at 37° C. for 24 and 48 hours. After incubation, the antimi- F52C3p, *Lactobacillus salivarius* F41C3p, *Streptococcus mitis* F3C2v and *Lactobacillus pentosus* or *plantarum* L1C1 bacteria were carried out on reconstituted epidermises of EpiSkin (SkinEthic) type (1.07 cm$^2$) aged 13 days. The inserts containing the epidermises were placed in a 12-well plate with 2 ml of maintenance medium and incubated for 24 hours at 35° C.±2° C. in order to regenerate the epidermises. After incubation, the maintenance medium was removed and 2 ml of MRS medium were added. A medium simulating wound exudates, called Simulated Wound Fluid (50/50 vol/vol) (described in Werthén et al., 2010) was then inoculated with the bacteria according to the invention (concentration of approximately 2.5×10$^7$ CFU·ml$^{-1}$). After 24 h of incubation, the bacteria which had not adhered were removed by washing with physiological saline. The epidermises were detached from the inserts with a scalpel and placed in a sterile container containing 9 ml of MRS medium. The bacteria that had adhered were detached by mechanical action (ultrasonic bath) and counted by dilution-plating on agar medium.

Figure 3:
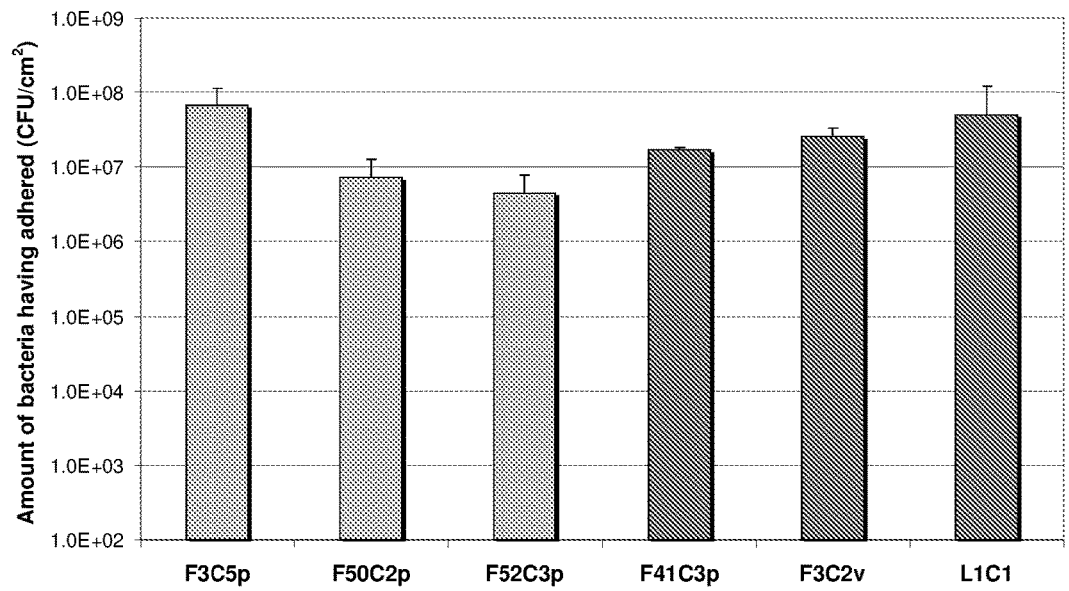
FIG. 3 represents the capacity of the bacteria according to the invention to adhere on reconstituted epidermises (as amount of bacteria adhered in $CFU/cm^2$).

The *Lactobacillus* saniviri F3C5p, *Lactobacillus salivarius* F50C2p, *Lactobacillus salivarius* F52C3p, *Lactobacillus salivarius* F41C3p, *Streptococcus mitis* F3C2v and *Lactobacillus pentosus* or *plantarum* L1C1 bacteria are capable of adhering to the epidermis and of persisting for 24 hours. The *Lactobacillus* saniviri F3C5p strain exhibits the greatest adhesion capacity (cf. FIG. 3).

EXAMPLE 4

Barrier effect—inhibition of pathogen adhesion on a collagen surface

The capacity of the *Lactobacillus* saniviri F3C5p, *Lactobacillus salivarius* F50C2p, *Lactobacillus salivarius* F52C3p, *Lactobacillus salivarius* F41C3p, *Streptococcus mitis* F3C2v and *Lactobacillus pentosus* or *plantarum* L1C1 bacterial strains to limit and/or inhibit the adhesion of pathogenic species (*S. aureus* MRSA ATCC 43300 or *P. aeruginosa* ATCC 9027) on matrices containing collagen was evaluated. The tests were carried out in 24-well microplates coated with type I collagen (BD Biocoat™ Collagen I).

The pathogenic bacteria were cultured for 16 hours at 37° C. in Tryptic Soy Broth (TSB) medium. After incubation, the cultures were diluted in TSB medium to concentrations of approximately $2.5 \times 10^7$ CFU·ml$^{-1}$, $2.5 \times 10^5$ CFU·ml$^{-1}$ and $2.5 \times 10^3$ CFU·ml$^{-1}$.

The *Lactobacillus* saniviri F3C5p, *Lactobacillus salivarius* F50C2p, *Lactobacillus salivarius* F52C3p, *Lactobacillus salivarius* F41C3p, *Streptococcus mitis* F3C2v and *Lactobacillus pentosus* or *plantarum* L1C1 bacteria were cultured in Man Rogosa Sharpe (MRS) medium for 16 hours, at 37° C. and under anaerobic conditions.

For the adhesion competition tests, the F3C5p, F50C2p and F52C3p bacteria and the pathogenic bacterium (*S. aureus* or *P. aeruginosa*) were simultaneously added at a respective concentration of approximately $2.5 \times 10^7$ CFU·ml$^{-1}$ and $2.5 \times 10^7$ CFU·ml$^{-1}$ or $2.5 \times 10^5$ CFU·ml$^{-1}$ or $2.5 \times 10^3$ CFU·ml$^{-1}$ for the pathogenic bacterium. The F41C3p, F3C2v and L1C1 bacteria and the pathogenic bacterium (*S. aureus* or *P. aeruginosa*) were simultaneously added at a respective concentration of approximately $2.5 \times 10^7$ CFU·ml$^{-1}$ and $2.5 \times 10^7$ CFU·ml$^{-1}$.

For the exclusion tests, the F3C5p, F50C2p and F52C3p bacteria were introduced into the wells at a concentration of approximately $2.5 \times 10^7$ CFU·ml$^{-1}$ and incubated at 37° C. for 24 hours. After adhesion, the wells were washed with physiological saline and the pathogenic strain (*S. aureus* or *P. aeruginosa*) was introduced into the wells at concentrations of approximately $2.5 \times 10^7$ CFU·ml$^{-1}$ or $2.5 \times 10^5$ CFU·ml$^{-1}$ or $2.5 \times 10^3$ CFU·ml$^{-1}$. The F41C3p, F3C2v and L1C1 bacteria were tested at a concentration of approximately $2.5 \times 10^7$ CFU·ml$^{-1}$ with the pathogenic strain (*S. aureus* or *P. aeruginosa*) at a concentration of approximately $2.5 \times 10^7$ CFU·ml$^{-1}$.

For each of the tests, after 24 hours of contact, the pathogenic bacteria were specifically counted on Baird-Parker medium supplemented with an emulsion of egg yolk containing potassium tellurite for *S. aureus* or cephalosporin/fucidin/cetrimide (CFC) medium for *P. aeruginosa*. After 24 h of incubation at 35° C.±2° C., the characteristic colonies were counted. A nontreated control with the bacteria according to the invention was carried out for each of the tests.

Figure 4:
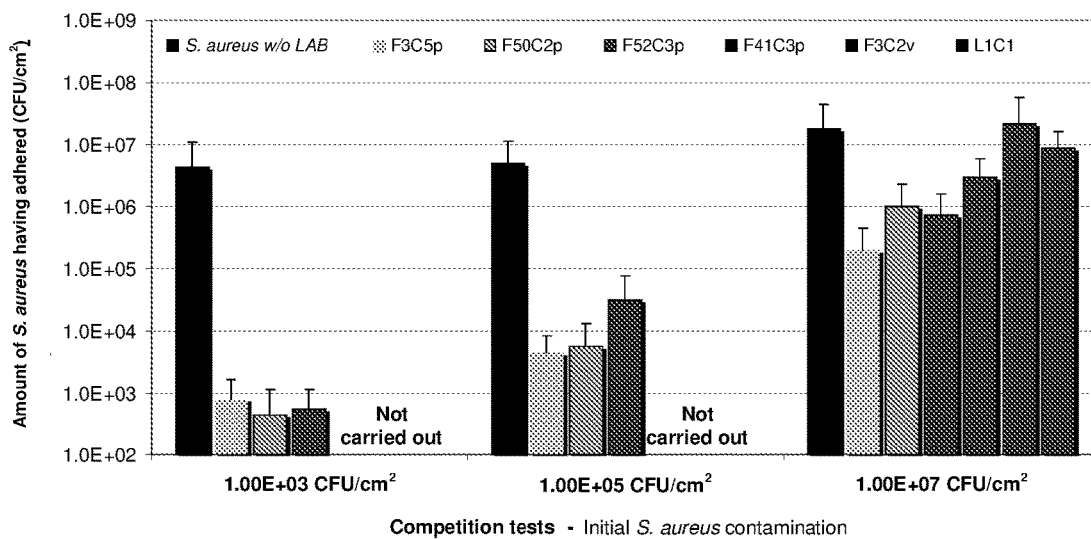
FIG. 4 represents the results of tests for competition of adhesion on collagen surfaces of the bacteria according to the invention with respect to *S. aureus* (amount of *S. aureus* adhered after 24 h of incubation ($CFU/cm^2$)).
Figure 5:
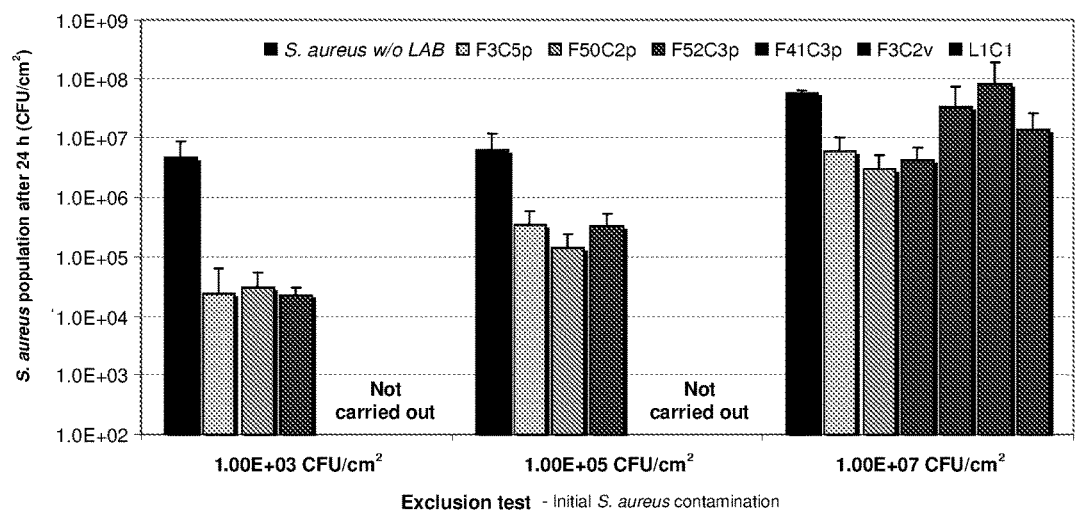
FIG. 5 represents the results of the tests for exclusion on collagen surfaces of the bacteria according to the invention with respect to *S. aureus* (amount of *S. aureus* after 24 h of incubation ($CFU/cm^2$)).

The F3C5p, F50C2p, F52C3p, F41C3p, F3C2v and L1C1 bacteria make it possible to strongly limit the adhesion of *S. aureus* and the colonization of the collagen-coated substrate compared with the nontreated control for the three concentrations tested (cf. FIGS. 4 and 5).

Figure 6:
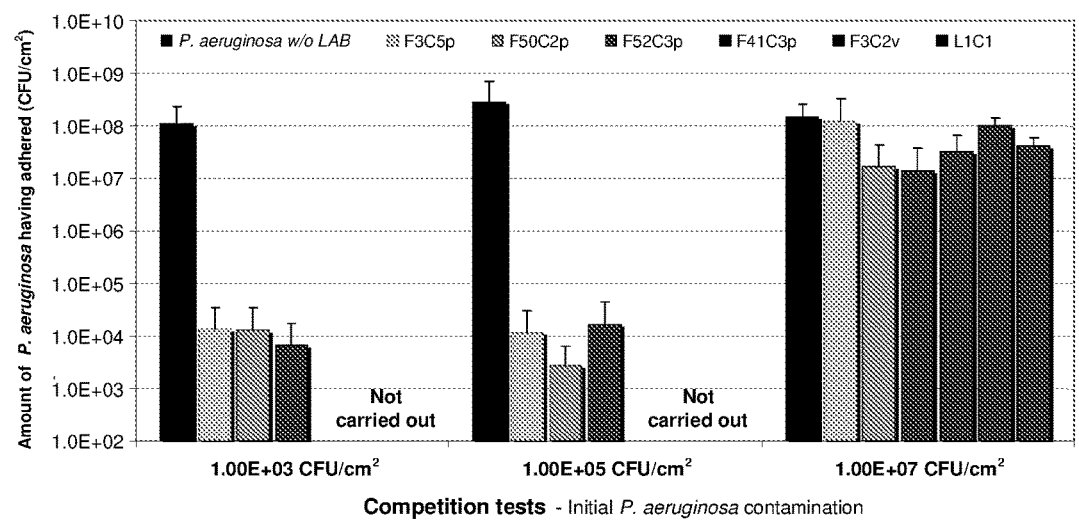
FIG. 6 represents the results of the tests for competition of adhesion on collagen surfaces of the bacteria according to the invention with respect to *P. aeruginosa* (amount of *P. aeruginosa* adhered after 24 h of incubation ($CFU/cm^2$)).
Figure 7:
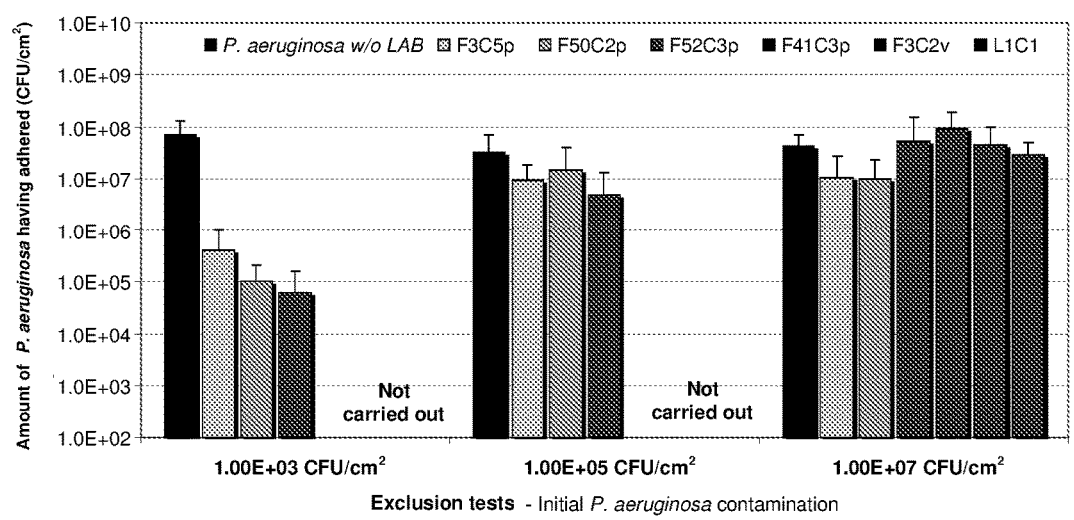
FIG. 7 represents the results of the tests for exclusion on collagen surfaces of the bacteria according to the invention with respect to *P. aeruginosa* (amount of *P. aeruginosa* after 24 h of incubation ($CFU/cm^2$)).
Figure 8A:
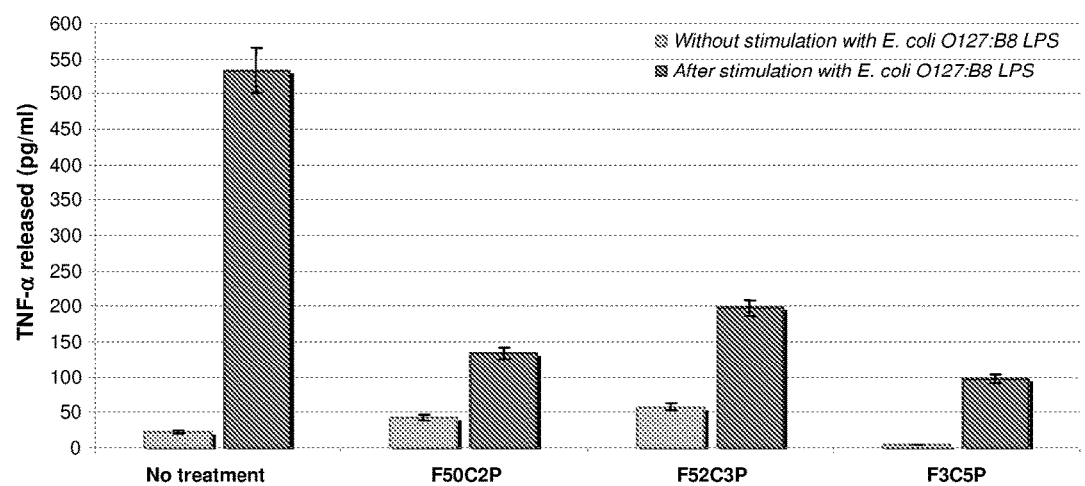
FIGS. 8a and 8b represent the amount of TNF-α released (pg/ml) by macrophages after 3.5 hours of contact with the bacteria according to the invention, without or with stimulation by LPS from *E. coli* O127:B8.
Figure 8B:
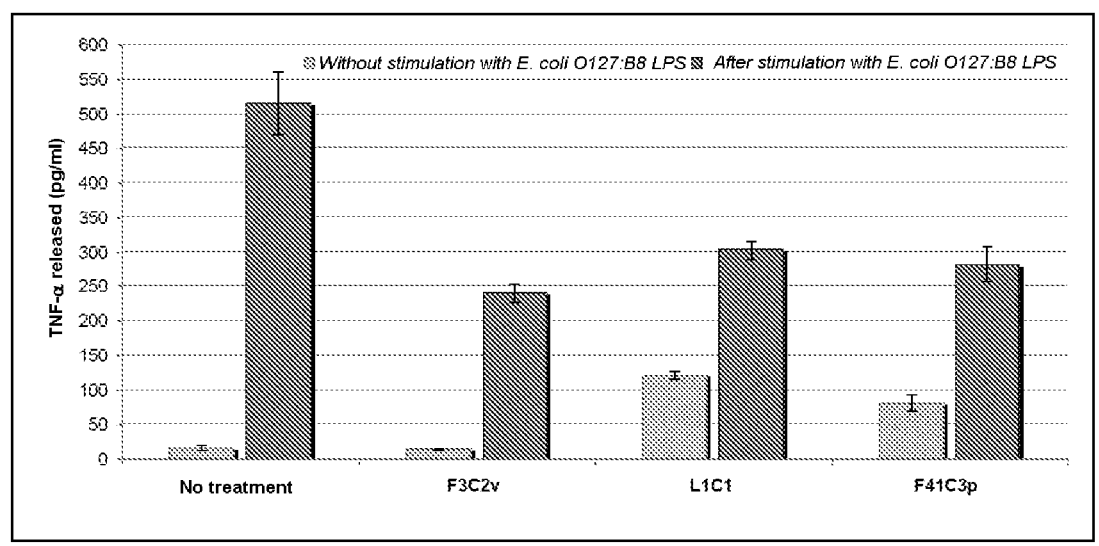

The F3C5p, F50C2p, F52C3p, F41C3p, F3C2v and L1C1 bacteria make it possible to limit the adhesion of *P. aeruginosa* and the colonization of the collagen-coated substrate compared with the nontreated control when the initial contamination is less than $10^5$ CFU/cm$^2$ (cf. FIGS. 6 and 7).

EXAMPLE 5

Immunomodulatory activities on macrophages

The *Lactobacillus* saniviri F3C5p, *Lactobacillus salivarius* F50C2p, *Lactobacillus salivarius* F52C3, *Lactobacillus pentosus/plantarum* L1C1, *Lactobacillus salivarius* F41C3p and *Streptococcus mitis* F3C2v strains were cultured in Man Rogosa Sharpe (MRS) medium for 16 hours, at 37° C. and under anaerobic conditions. The bacteria were recovered by centrifugation and then ultrasound-inactivated or heat-inactivated (95° C.) in order to obtain bacterial extracts.

THP1 monocyte cells (ATCC TIB-202) were cultured in Roswell Park Memorial Institute (RPMI) medium and were differentiated to macrophages by addition of phorbol-12-myristate-13-acetate (PMA). After 24 hours of culture, the macrophages obtained were exposed (i) either to the bacterial extracts alone, (ii) or to LPS from *E. coli* O127:B8, (iii) or to LPS from *E. coli* O127:B8 in the presence of cell extract. After 3.5 hours of contact, the concentration of tumor necrosis factor (TNF-α) was measured in the culture supernatant using an ELISA method.

The addition of the bacterial extracts alone does not induce any significant release of TNF-α compared with the control not containing cell extract and therefore does not induce any pro-inflammatory reaction, with the exception of the L1C1 strain, which induces a weak release of TNF-α (concentration of 121 pg/ml).

The stimulation of the macrophages with the LPS from *E. coli* brings about a considerable release of TNF-α in the absence of bacterial extracts (concentration about 500 pg/ml). The simultaneous addition of the cell extracts prepared from the various bacterial strains (F3C5p, F41C3p, F50C2p, F52C3p, L1C1 or F3C2v) with the LPS makes it possible to significantly reduce (by a factor of 2 to 5) the release of TNF-α by the macrophages. These results demonstrate the anti-inflammatory potential of the 6 strains of lactic acid bacteria.

The references cited in the present application are the following:

1 Brachkova M I, Marques P, Rocha J, Sepodes B, Duarte M A, Pinto J F (2011). Alginate films containing *Lactobacillus plantarum* as wound dressing for prevention of burn infection. J. Hosp. Infect. 79: 375-377
2 Costerton, J. W., Stewart, P. S. and Greenberg, E. P. (1999). Bacterial biofilms: a common cause of persistent infections. Science 284 (5418): 1318-1322
3 Gan B S, Kim J, Reid G, Cadieux P, Howard J C (2002). *Lactobacillus fermentum* RC-14 inhibits *Staphylococcus aureus* infection of surgical implants in rats. J. Infect. Dis. 185: 1369-1372
4 Gueniche A, Hennino A, Goujon C, Dahel K, Bastien P, Martin R, Jourdain R, Breton L (2006). Improvement of atopic dermatitis skin symptoms by *Vitreoscilla filiformis* bacterial extract. Eur. J. Dermatol. 16: 380-384
5 Gueniche A, Buetler T, Benyacoub J, Blum S (2008a). *Lactobacillus johnsonii* provides a dose-dependent protection against UVR-induced immunosuppression. Eur. J. Dermatol. 18: 476-477
6 Gueniche A, Cathelineau A C, Bastien P, Esdaile J, Martin R, Queille Roussel C, Breton L (2008b). *Vitreoscilla* filiformis biomass improves seborrheic dermatitis. J. Eur. Acad. Dermatol. Venereol. 22: 1014-1015
7 Gueniche A, Dahel K, Bastien P, Martin R, Nicolas J F, Breton L (2008c). *Vitreoscilla filiformis* bacterial extract to improve the efficacy of emollient used in atopic dermatitis symptoms. J. Eur. Acad. Dermatol. Venereol. 22: 746-747
8 Gueniche A, Knaudt B, Schuck E, Volz T, Bastien P, Martin R, Rocken M, Breton L, Biedermann T (2008d). Effects of nonpathogenic gram-negative bacterium *Vitreoscilla filiformis* lysate on atopic dermatitis: a prospective, randomized, double-blind, placebo-controlled clinical study. Br. J. Dermatol. 159: 1357-1363
9 Gueniche A, Bastien P, Ovigne J M, Kermici M, Courchay G, Chevalier V, Breton L, Castiel-Higounenc I (2009). *Bifidobacterium longum* lysate, a new ingredient for reactive skin. Exp. Dermatol. 19: e1-8
10 Gueniche A, Benyacoub J, Philippe D, Bastien P, Kusy N, Breton L, Blum S, Castiel-Higounenc I (2010). *Lactobacillus paracasei* CNCM 1-2116 (ST11) inhibits substance P-induced skin inflammation and accelerates skin barrier function recovery in vitro. Eur. J. Dermatol. 20: 731-737
11 Halper J, Leshin L S, Lewis S J, Li W I (2003). Wound healing and angiogenic properties of supernatants from *Lactobacillus* cultures. Exp Biol Med 228: 1329-1337
12 Oh S, Kim S H, Ko Y, Sim J H, Kim K S, Lee S H, Park S, Kim Y J (2006). Effect of bacteriocin produced by *Lactococcus* sp. H Y 449 on skin-inflammatory bacteria. Food and Chemical Toxicology 44 (2006) 1184-1190
13 Im E, Choi Y J, Kim C H, Fiocchi C, Pothoulakis C, Rhee S H (2009). The angiogenic effect of probiotic *Bacillus polyfermenticus* on human intestinal microvascular endothelial cells is mediated by IL-8. Am. J. Physiol. Gastrointest. Liver Physiol. 297: G999-G1008
14 Mi-Sun Kang M S, Oh J S, Lee S W, Lim H S, Choi N K, and Kim S M (2012). Effect of *Lactobacillus reuteri* on the proliferation of *Propionibacterium acnes* and *Staphylococcus epidermidis*. The Journal of Microbiology (2012) Vol. 50, No. 1, pp. 137-142
15 Peral M C, Martinez M A, Valdez J C (2009). Bacteriotherapy with *Lactobacillus plantarum* in burns. Int. Wound J. 6: 73-81
16 Peral M C, Rachid M M, Gobbato N M, Huaman Martinez M A, Valdez J C (2010). Interleukin-8 production by polymorphonuclear leukocytes from patients with chronic infected leg ulcers treated with *Lactobacillus plantarum*. Clin. Microbiol. Infect. 16: 281-286
17 Ramos A N, Gobbato N, Rachid M, Gonzalez L, Yantorno O, Valdez J C (2010). Effect of *Lactobacillus plantarum* and *Pseudomonas aeruginosa* culture supernatants on polymorphonuclear damage and inflammatory response. Int. Immunopharmacol. 10: 247-251
18 Sikorska H, Smoragiewiczb W (2013). Role of probiotics in the prevention and treatment of meticillin-resistant *Staphylococcus aureus* infections. International Journal of Antimicrobial Agents 42 (2013) 475-481
19 Valdez J C, Peral M C, Rachid M, Santana M, Perdigon G (2005). Interference of *Lactobacillus plantarum* with *Pseudomonas aeruginosa* in vitro and in infected burns: the potential use of probiotics in wound treatment. Clin. Microbiol. Infect. 11: 472-479
20 Alberto N. Ramos, Maria E. Sesto Cabral, Diego Noseda, Alejandra Bosch, Osvaldo M. Yantorno, Juan C. Valdez, (2012). Antipathogenic properties of *Lactobacillus plantarum* on *Pseudomonas aeruginosa*: The potential use of its supernatants in the treatment of infected chronic wounds. Wound Rep Reg (2012)

The invention claimed is:

1. A method for preventing and/or treating an infection and/or a colonization related to at least one bacterium or one yeast chosen from *S. aureus, P. aeruginosa, Streptococcus pyogenes, Enterococcus faecium, Enterobacter cloacae, Proteus mirabilis, Bacteroides fragilis, Staphylococcus epidermidis, Propionibacterium acnes, Candida albicans* and *Malassezia furfur* comprising the administration to a subject in need thereof of at least one bacterium chosen from *Lactobacillus saniviri* registered on Jul. 12, 2012, at the CNCM under No. I-4650, *Lactobacillus salivarius* registered on Jul. 12, 2012, at the CNCM respectively under Nos. I-4651, I-4652 and I-4653, *Streptococcus mitis* registered on Jul. 12, 2012, under No. CNCM I-4654 and *Lactobacillus pentosus* or *plantarum* registered on Jul. 12, 2012, under No. CNCM I-4655.

2. The method according to claim 1, wherein the infection and/or the colonization is related to *S. aureus* and/or *P. aeruginosa*.

3. The method according to claim 1, wherein the administrated bacterium is an immunomodulator.

4. The method according to claim 1, wherein the administrated bacterium is applied to the skin, wounds, mucosae and/or superficial body growths.

5. The method according to claim 1, wherein in that the infection and/or the colonization concern the skin or a wound.

6. The method according to claim 5, wherein the wound is chosen from diabetic foot ulcers, leg ulcers of arterial origin, leg ulcers of venous origin, bedsores, whitlow, acute wounds, traumatic wounds and post-operative wounds.

7. The method according to claim 1, further comprising the administration of at least one compound chosen from probiotics, prebiotics and yeasts.

8. The method according to claim 1, further comprising the administration of at least one active agent chosen from antifungal agents, painkillers, antiinflammatories, active agents which promote healing, moisturizing agents, keratolytic agents, restructuring agents and anesthetics.

9. The method according to claim 1, wherein the bacterium is suitable for topical, oral or parenteral application.

10. The method according to claim 1, wherein the bacterium is administrated in the form of a salve, a cream, a milk, an ointment, a powder, an impregnated pad, a syndet, a wipe, a solution, a gel, a spray, a foam, a suspension, a lotion, a stick, a shampoo, a washing base, a tablet, a gel capsule, a food product or an injectable solution.

11. The method according to claim 1, wherein the bacterium is administrated in an amount of between $10^3$ and $10^{12}$ bacteria cells.

12. The method according to claim 1, wherein the bacterium is present in the form of an inactivated cell, a living cell or a cell lysate, which may be encapsulated or nonencapsulated, immobilized or nonimmobilized and lyophilized or nonlyophilized.

* * * * *